(12) United States Patent
Matsukawa

(10) Patent No.: US 9,090,710 B2
(45) Date of Patent: Jul. 28, 2015

(54) METHOD OF ARRAYING FERRITIN

(75) Inventor: Nozomu Matsukawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 906 days.

(21) Appl. No.: 13/299,737

(22) Filed: Nov. 18, 2011

(65) Prior Publication Data

US 2012/0116061 A1    May 10, 2012

Related U.S. Application Data

(63) Continuation of application No. PCT/JP2009/005204, filed on Oct. 7, 2009.

(30) Foreign Application Priority Data

May 21, 2009   (JP) .................................. 2009-122867

(51) Int. Cl.
| | | |
|---|---|---|
| *C07K 14/79* | (2006.01) | |
| *B82Y 40/00* | (2011.01) | |
| *C07K 14/47* | (2006.01) | |

(52) U.S. Cl.
CPC ................. *C07K 14/79* (2013.01); *B82Y 40/00* (2013.01); *C07K 14/47* (2013.01)

(58) Field of Classification Search
None
See application file for complete search history.

(56) References Cited

U.S. PATENT DOCUMENTS

| | | |
|---|---|---|
| 2003/0198812 A1 | 10/2003 | Rueckes et al. |
| 2006/0257931 A1 | 11/2006 | Yamashita et al. |
| 2008/0154024 A1 | 6/2008 | Kirimura et al. |
| 2012/0122669 A1* | 5/2012 | Matsukawa .................. 502/246 |

FOREIGN PATENT DOCUMENTS

| | | |
|---|---|---|
| JP | 2008-054599 | 3/2008 |
| JP | 2009-007339 | 1/2009 |

OTHER PUBLICATIONS

Ken-Ichi Sano et al., "A Hexapeptide Motif that Electrostatically Binds to the Surface of Titanium," J.A.C.S Communications, 125, 14234 (2003).
Ken-Ichi Sano et al., "Specificity and Biomineralization Activities of Ti-Binding Peptide-1 (TBP-1)," Langumir 2005, vol. 21, pp. 3090-3095.
Ichio Yamashita et al., "Selective Nanoscale Positioning of Ferritin and Nanoparticles by Means of Target-Specific Peptides," Small, 2, No. 10, pp. 1148-1152, 2006.
Tomohiro Hayashi et al., "Mechanism Underlying Specificity of Proteins Targeting Inorganic Materials," Nano Letters, vol. 6, No. 3, pp. 515-519, 2006.
Shinya Kumagai et al., "Electrostatic placement of single ferritin molecules," Applied Physics Letters, 88, 153103 (2006).
Ken-Ichi Sano et al., "In Aqua Manufacturing of a Three-Dimensional Nanostructure Using a Peptide Aptamer," MRS Bulletin vol. 33, May 2008, pp. 524-529.
Kenneth Douglas et al., "Biomolecular/solid-state nanoheterostructures," Appl. Physi. Letters vol. 56, No. 7, Feb. 1990, pp. 692-694.

* cited by examiner

*Primary Examiner* — Anand Desai
(74) *Attorney, Agent, or Firm* — McDermott Will & Emery LLP

(57) ABSTRACT

A method of selectively arraying ferritin and inorganic particles on a silicon oxide substrate at regions having vanadium, niobium or tantalum. An aspect of the method includes steps of: preparing a solution which contains ferritin modified at an N-terminal part of a subunit with a peptide set out in SEQ ID NO: 1, and from 0.01 v/v % to 10 v/v % of a nonionic surfactant and having a pH of from 7.4 to 8.2; and a binding step of bringing the solution in contact with regions of the substrate having vanadium, niobium, or tantalum to selectively array peptide-modified ferritin to vanadium, niobium or, tantalum portion. The method may also include a step of selectively arraying ferritin modified with the peptide set out in SEQ ID NO: 1, and the inorganic particles contained in ferritin at the vanadium, niobium, or tantalum portion by removing the solution.

5 Claims, 8 Drawing Sheets

Number of minT1-LF adsorbed (200 x 200 nm²)

Number of minT1-LF adsorbed on Silicon oxide (200 × 200 nm²)

METHOD OF ARRAYING FERRITIN

RELATED APPLICATIONS

This is a continuation of PCT International Application No. PCT/JP2009/005204, filed on Oct. 7, 2009, claiming priority of Japanese Patent Application No. 2009-122867, filed on May 21, 2009, the disclosures of which Applications are hereby incorporated by reference.

SEQUENCE LISTING

The Sequence listing in "SEQUENCE LISTING.TXT" created on Jan. 23, 2012 being 3.12 KB in size is incorporated by reference.

TECHNICAL FIELD

The present invention relates to a method of selectively arraying ferritin at a vanadium, niobium, or tantalum portion formed on a silicon oxide substrate. The present invention also relates to a method of selectively arraying inorganic particles contained in ferritin on a silicon oxide substrate at a vanadium, niobium, or tantalum portion.

BACKGROUND ART

In known conventional methods for arraying ferritin or inorganic particles contained in ferritin on a solid, arraying is carried out by way of electrostatic interaction on a pattern having electrostatically reversed polarity produced by a lithography technique (for example, see NPL 5).

NPL 5 discloses: applying a resist on a silicon oxide substrate; developing the resist in areas exposed with electron beam lithography to remove the resist; exposing the areas on which the silicon oxide substrate was exposed to a vapor of a silane coupling agent having an amino group attached to the end, specifically, vapor of aminopropyltrimethoxysilane, so as to allow an amino-terminal silane coupling agent to be adsorbed only to the exposed areas; and then removing the resist with a solvent to form a pattern by amino-terminal silane coupling on a part of the silicon oxide substrate, in which arraying ferritin only on an amino-terminal silane coupling-modified pattern is enabled by controlling electrostatic interaction by adjusting the pH and the ionic strength.

A method in which modification of a ferritin surface with a peptide consisting of six amino acids (arginine-lysine-leucine-proline-aspartic acid-alanine: hereinafter, denoted as RKLPDA in terms of one letter code) selected so as to provide an affinity to titanium (see NPL 1) imparts to ferritin an affinity to titanium, and further interaction with the solid surface is weakened using a nonionic surfactant to permit selective array on a titanium pattern (see PTL 1, and NPL 3) is also known.

NPL 4 discloses an increase in selection ratio resulting from the difference of amounts of adsorption of the nonionic surfactant in selective array on titanium by way of the peptide RKLPDA. NPL 4 discloses that a larger amount of the nonionic surfactant is adsorbed on hydrophobic substrates and silicon substrates as compared with titanium substrates. NPL 4 suggests that a large amount of nonionic surfactant would be adsorbed as long as the substrate is hydrophobic. However, NPL 4 fails to disclose any mechanism of occurrence of the difference of adsorption on the hydrophilic substrate, titanium, and on silicon.

On the other hand, PTL 2 discloses a method of selective arraying ferritin on titanium or silicon nitride on platinum or silicon oxide by way of only the difference of amounts of adsorption of a nonionic surfactant. Materials which may be an affinity target of the peptide RKLPDA are disclosed in NPL 2. NPL 2 discloses that the peptide RKLPDA has affinities to titanium, silicon, and silver, whereas it does not have affinities to gold, chromium, platinum, tin, zinc, copper, and iron.

In brief, it has been known so far that nonionic surfactants have an effect of weakening the interaction between a protein and a substrate, the difference of amounts of adsorption on a solid surface enables protein array on hydrophobic surfaces such as gold and platinum as well as on silicon oxide surface to be selectively inhibited, and that modification of a protein surface with a peptide RKLPDA enables affinities to titanium, silicon and silver to be imparted.

CITATION LIST

Patent Literature

[PTL 1]
PCT International Publication No. 2006/064639
[PTL 2]
PCT International Publication No. 2006/064640

Nonpatent Literature

[NPL 1]
Kenichi Sano, Kiyotake Shiba, J.A.C.S., 125, 14234 (2003)
[NPL 2]
Kenichi Sano, Hiroyuki Sasaki, Kiyotake Shiba, Langmuir, 21, 3090 (2005)
[NPL 3]
Ichiro Yamashita, Hiroya Kirimura, Mitsuhiro Okuda, Kazuaki Nishio, Ken-Ichi Sano, Kiyotake Shiba, Tomohiro Hayashi, Masahiko Hara, Yumiko Mishima, Small, 2, 1148 (2006)
[NPL 4]
Tomohiro Hayashi, Kenichi Sano, Kiyotake Shiba, Yoshikazu Kumashiro, Kenji Iwahori, Ichiro Yamashita, Masahiko Hara, Nano Letters, 6, 515 (2006)
[NPL 5]
Shinya Kumagai, Shigeo Yoshii, Kiyohito Yamada, Nozomu Matsukawa, Isamu Fujiwara, Kenji Iwahori, Ichiro Yamashita, Applied Physics Letters, 88, 153103 (2006)

SUMMARY OF INVENTION

Technical Problem

For using inorganic nanoparticles as a semiconductor device or catalyst, it is necessary to array the inorganic nanoparticles on a silicon substrate selectively, or at a portion of a metal element such as vanadium, niobium, or tantalum in a silica matrix at a high density. However, in the conventional method carried out using electrostatic interaction, patterning by lithography is required, and a coupling agent capable of adsorbing on a surface other than silicon at a high density is necessary.

In this regard, the peptide RKLPDA has been known to have affinities to titanium, silicon, and silver, whereas it has been known to lack affinities to many elements such as gold, chromium, platinum, tin, zinc, copper, and iron. In addition, for selective arraying of a protein modified with the peptide RKLPDA at desired elements on silicon having an affinity to the peptide RKLPDA, it is necessary to achieve both suppression of the affinity of the protein to the silicon surface and adsorption of the protein to the desired elements.

Solution to Problem

The method of the present invention in order to solve the foregoing conventional problems is
a method of arraying ferritin, the method comprising steps of:
a preparing step of preparing a solution containing ferritin modified at an N-terminal of a subunit with a peptide set out in SEQ ID NO: 1, and from 0.01 v/v % to 10 v/v % of a nonionic surfactant, wherein the solution has a pH falling within the range of from 7.4 to 8.2; and
a binding step of bringing the solution in contact with a silicon oxide substrate having a metal portion selected from vanadium, niobium, and tantalum formed on a part of the surface so as to selectively bind the ferritin to the metal portion.

In this method, modifying ferritin at an N-terminal of a subunit with a peptide includes any of: substituting an N-terminal amino acid residue (methionine residue) of ferritin with the peptide set out in SEQ ID NO: 1; adding the peptide set out in SEQ ID NO: 1 to the N-terminal of ferritin; and inserting the peptide set out in SEQ ID NO: 1 into the amino acid sequence of the N-terminal of ferritin.

It is preferred that the method further comprises after the binding step, a removal step of removing the solution to leave the ferritin selectively bound to the metal portion on the silicon oxide substrate.

It is also preferred that the method further comprises after the binding step, a cleaning step of washing the surface of the silicon oxide substrate with a solution not containing the ferritin so as to leave the ferritin selectively bound to the metal portion on the silicon oxide substrate.

In the method of arraying ferritin of the present invention, the ferritin may contain inorganic particles. It is preferred that the method further comprises after the binding step, a degradation step of heating the silicon oxide substrate to decompose the ferritin to array the inorganic particles which had been in the ferritin at the metal portion on the silicon oxide substrate.

Ferritin is oxidized and decomposed when subjected to a heat treatment in a nitrogen atmosphere at not lower than 500° C., in an oxygen atmosphere at not lower than 400° C., or in an ozone atmosphere at not lower than 110° C.; however, inorganic particles are left. Therefore, when inorganic particles are contained in peptide-modified ferritin, selectively arraying ferritin at a vanadium, niobium, or tantalum portion on silicon oxide, followed by subjecting to a heat treatment to remove the ferritin by decomposition enables selective array of only the inorganic particles at a vanadium, niobium, or tantalum portion.

Note that since an adsorption process of in a solution is employed in the method of arraying ferritin of the present invention, even if a structure is formed on a substrate, it is substantially the same as the case of a flat substrate in the area where a solution can be in contact.

The objects described in the foregoing, other objects, features and advantages of the present invention will be apparent from the following detailed description of preferred embodiments with reference to attached drawings.

Advantageous Effects of Invention

According to the method of arraying ferritin of the present invention, selectively arraying ferritin, in turn, inorganic particles contained in ferritin at a vanadium, niobium, or tantalum portion formed on a part of silicon oxide can be realized.

DESCRIPTION OF EMBODIMENTS

Figure 1:
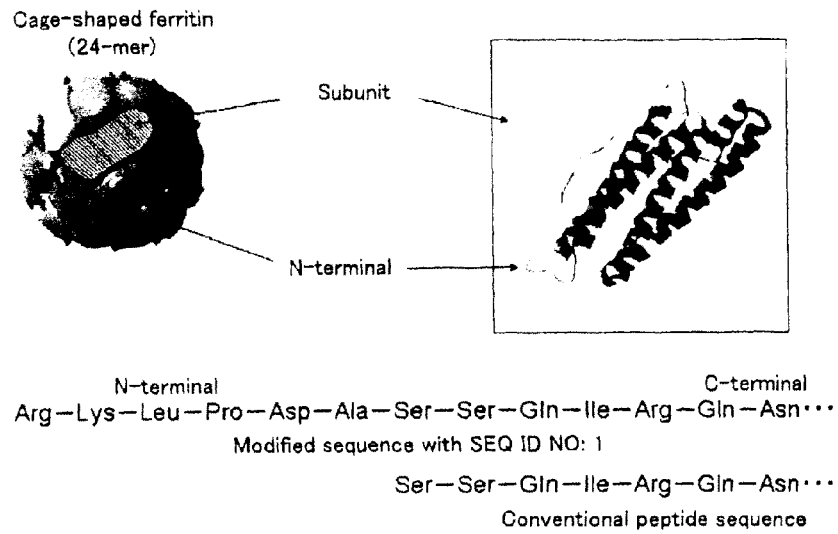
FIG. 1 shows a schematic view illustrating a relationship between cage-shaped ferritin and subunits, and the N-terminal.

Hereinafter, preferred modes for carrying out the invention are explained in detail.

Ferritin used in the present invention has an amino acid sequence set out in SEQ ID NO: 1 at the N-terminal of the subunit. In exemplary ferritin used in the present invention, methionine corresponding to an N-terminal start codon of the protein set out in SEQ ID NO: 3 is substituted with an amino acid sequence set out in SEQ ID NO: 1. Since the expression system used in this embodiment lacks methionine corresponding to the start codon, this protein consists of 180 residues, having a 174-residue amino acid sequence of horse-derived ferritin, which lacks methionine from SEQ ID NO: 3, modified at the amino terminal with a 6-residue amino acid sequence set out in SEQ ID NO: 1.

In Experiment Example which is described later, ferritin in which SEQ ID NO: 1 is modified is denoted as "minT1-LF". As a general ferritin employed in Comparative Example, the ferritin consisting of 174 residues, which lacks methionine from SEQ ID NO: 3, was used. Hereinafter, the general ferritin is denoted as "Δ1-LF".

The substrate employed was a thermally oxidized silicon substrate having a pattern partially formed thereon of a metal element selective array of which was intended. The substrate was cleaned immediately before using. For the cleaning, water washing, organic solvent washing, and a treatment with UV ozone were sequentially carried out.

The method of selective arraying ferritin of the present invention predominantly has three steps, i.e., a preparation step, a binding step, and a removal step.

(1) Regarding Preparation Step
In the preparation step, a solution is prepared which contains ferritin modified at an N-terminal of a subunit with a peptide set out in SEQ ID NO: 1, and from 0.01 v/v % to 10 v/v % of a nonionic surfactant and which has a pH falling within the range of from 7.4 to 8.2.

(2) Regarding Binding Step

In the binding step, the solution containing ferritin and the nonionic surfactant prepared in the preparation step is added dropwise on a silicon oxide substrate.

(3) Regarding Removal Step

The removal step is carried out for the purpose of removing remaining ferritin in the solution which had been brought in contact with the silicon oxide substrate. There are mainly two methods of removal, one being removing the solution by centrifugation while inhibiting drying, and another being washing away to remove with a solution not containing ferritin. According to the removal by centrifugation, ferritin may remain unremoved due to the irregularity of the substrate surface; therefore, the process of washing away with a solution not containing ferritin is preferred.

Accordingly, the arraying of the ferritin on a substrate is achieved. It should be noted that when ferritin containing inorganic particles is used as the ferritin, arraying the inorganic particles on a substrate is enabled by degrading ferritin.

Examples of the present invention are explained in more detail in the following.

Example 1

First, a method of producing ferritin used in Examples below is explained. In Examples of the present application, recombinant ferritin "minT1-LF" modified with a polypeptide set out in SEQ ID NO: 1 at the N-terminal, and recombinant ferritin "Δ1-LF" not having the sequence set out in SEQ ID NO: 1 were used.

<Method of Producing Δ1-LF>

First, a method of producing Δ1-LF is explained. Since there are L-type and H-type subunits of natural horse spleen-derived ferritin having slightly different structures, natural ferritin does not have a certain structure. Thus, in Examples of the present application, recombinant ferritin consisting only of the L-type subunit was used.

The DNA (SEQ ID NO: 2; 528 base pairs) coding for L-type ferritin was first amplified using a PCR method to provide a large amount of L-type ferritin DNA. Next, this L-type ferritin DNA was cut at specific sites (restriction enzyme sites) with restriction enzymes EcoRI and HindIII. A solution of an L-type ferritin DNA fragment having restriction enzyme sites for EcoRI and HindIII was prepared by this cutting treatment. This solution was subjected to DNA electrophoresis, and only a DNA fragment coding for L-type ferritin was recovered and purified.

Thereafter, this L-type ferritin DNA fragment, and a vector plasmid (pMK-2) which had been treated with EcoRI-HindIII restriction enzymes were incubated to carry out ligation. Thus, a vector plasmid pMK-2-fer-0 was produced in which L-type ferritin DNA was incorporated into a multicloning site (MSC) of pMK-2 plasmid. The vector plasmid pMK-2 was selected since it is advantageous in obtaining a large amount of ferritin due to having Tac promoter as a promoter, and a characteristic feature of many copy number as a multicopy plasmid.

Figure 2:
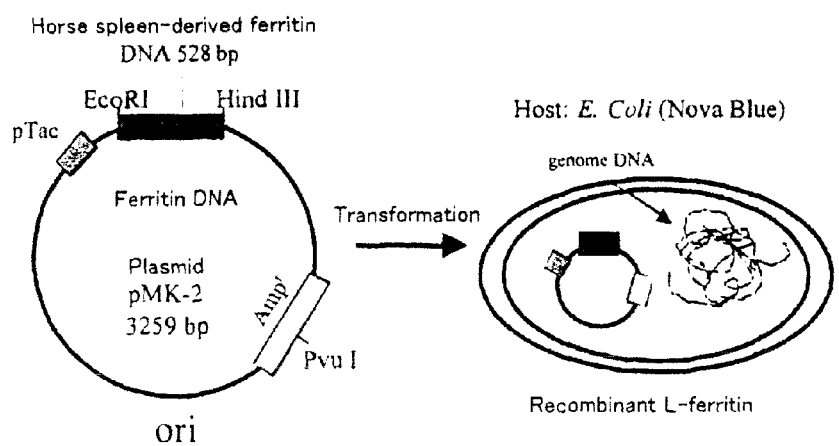
FIG. 2 shows a schematic view illustrating main construction of a plasmid of an L-type ferritin subunit, and incorporation of the plasmid into *Escherichia coli*.

Thus produced plasmid (pMK-2-fer-0) was introduced (transfected) into a host *Escherichia coli* strain, *E. coli* Nova Blue (Novagen) to produce a recombinant L-type ferritin strain (Δ1-LF). Note that main construction of the plasmid of L-type ferritin subunit, and a schematic drawing showing incorporation of the plasmid into *Escherichia coli* are shown in FIG. 2.

Inorganic particles were contained into the interior of these recombinant ferritin by the method described later.

<Method of Producing minT1-LF>

Next, a method of producing ferritin (minT1-LF) modified with SEQ ID NO: 1 at the N-terminal is explained.

When the amino terminal (N-terminal) of the subunit constructing ferritin is modified with the peptide, a structure is provided in which the peptide overhangs the external side of the ferritin particle as shown in FIG. 1. Thus, by modifying this N-terminal part with an optional peptide, modification of the surface of ferritin particles with the peptide is enabled.

Next, specific method of producing the minT1-LF is explained hereafter. A full length gene of an L-type subunit of natural ferritin (derived from horse liver) is set out in SEQ ID NO: 2. Since the expression system used in this Example lacks methionine corresponding to a start codon, ferritin consisting of 174-residue amino acid excluding methionine from ferritin having the amino acid sequence set out in SEQ ID NO: 3 is synthesized from the DNA set out in SEQ ID NO: 2.

First, DNAs coding for SEQ ID NO: 1 (SEQ ID NO: 4 (30 base pairs) and SEQ ID NO: 5 (22 base pairs)) were amplified with a PCR method to provide a large amount of DNA.

Next, the DNA, and a vector plasmid (pMK-2) coding for recombinant L-type ferritin which had been treated with restriction enzymes Bam I and Sac I were incubated to carry out ligation. Thus, a vector plasmid (pKIS1) was produced in which the DNA having the aforementioned base sequence and L-type ferritin DNA were incorporated into a multicloning site (MSC) of pMK-2 plasmid. The vector plasmid pMK-2 used in producing pKIS1 promoter was selected since it is advantageous in obtaining a large amount of ferritin due to having Tac promoter as a promoter, and a characteristic feature of many copy number as a multicopy plasmid.

Thus the produced plasmid was introduced (transformed) into a host *Escherichia coli* strain, *E. coli* XLI Blue (Novagen) to produce an L-type ferritin strain (minT1-LF) modified with the polypeptide set out in SEQ ID NO: 1 at the N-terminal.

<Introduction of Inorganic Particles into minT1-LF>

Although the type of inorganic particles contained in ferritin is not particularly limited in the present invention, ferric oxide ($Fe_2O_3$) was used as the inorganic particle in Examples. Introduction of $Fe_2O_3$ core into the minT1-LF was performed as in the following.

As a reaction solution, 0.5 mg/mL minT1-LF/100 mM HEPES-NaOH (pH 7.0) was prepared, and thereto was added 5 mM ammonium iron acetate. The reaction was allowed at 25° C. overnight, and the minT1-LF having a $Fe_2O_3$ core formed therein was subjected to molecular purification by centrifugal separation and gel filtration from the solution after completing the reaction, and then recovered. The centrifugal separation was carried out stepwise under conditions at 1,600 G for 10 min and at 10,000 G for 30 min to remove unnecessary portions other than the minT1-LF as precipitates. The minT1-LF having a $Fe_2O_3$ core formed therein was recovered from finally remaining supernatant as pellets by ultracentrifugal separation at 230,000 G for 1 hour.

The minT1-LF thus obtained was subjected to gel filtration using HPLC (column: TSK-GEL G4000WXL PEEK; flow rate: 1 ml/min; buffer: 50 mM Tris-HCl (pH 8.0)+150 mM NaCl), and a peak of a 24-mer (about 480 kDa) was fractionated. The minT1-LF solution thus fractionated was concentrated using an ultrafiltration membrane to obtain the minT1-LF containing $Fe_2O_3$.

In addition, by carrying out a similar operation to the above-described operation with Δ1-LF, Δ1-LF containing $Fe_2O_3$ therein was obtained.

<Method of Producing Substrate>

Next, a method of producing a substrate used in Examples of the present application is explained.

A resist (Nippon ZEON Co., Ltd.: ZEP520) was applied on one half of a 10 mm×square thermally oxidized silicon substrate, and baked at 140° C. for 3 min. Thereafter, a metal thin film was formed by RF magnetron sputtering with a metal element as a target. The target employed was vanadium, niobium, or tantalum having a purity of not less than 99.5% (Kojundo Chemical Laboratory Co., Ltd.,). In order to eliminate influences from the difference in level, the thickness was predetermined to be 1 nm.

The metal thin film on the resist was removed by ultrasonic cleaning in a remover (Nippon ZEON Co., Ltd.: dimethylacetamide) heated to 40° C. to produce a substrate having silicon oxide on a half surface, and vanadium, niobium, or tantalum on the other half surface.

In order to confirm that selective array in a nano-order size is enabled; a substrate having thin lines patterned thereon was also produced by electron beam lithography. On a 10 mm×square thermally oxidized silicon substrate was applied a 300-Å resist (Nippon ZEON Co., Ltd.: ZEP520) by spin coating, and thereafter baked at 140° C. for 3 min. The thin lines were exposed by electron beam lithography (Elionix Inc.: ELS-7500), and developed with a developing solution (Nippon ZEON Co., Ltd.: n-amyl acetate) to produce a substrate on which the surface having a thin line area (width 20 nm×length 200 nm) was exposed. In the following procedure, thin lines of tantalum were produced in a similar manner to the production of the half surface-processed substrate.

The surface of the substrate thus produced was cleaned for use immediately before using by ultrasonic cleaning in (1) ultra-pure water, (2) ethanol of electronic industrial grade, and (3) acetone of electronic industrial grade, in sequence, and thereafter in an UV ozonizer while heating at 110° C.

The substrate after washing as described above was subjected to surface measurement with an atomic force microscope, and confirmed that the vanadium, niobium or tantalum portion produced on the substrate were a flat thin film, and that the thin film had a thickness of no greater than 2 nm.

<Preparation of Solution>

Next, a method of preparing a solution used in Examples of the present application is explained.

First, a 50 mM buffer (pH 7.8) was prepared using ultra-pure water (Millipore), MES (Sigma-Aldrich), and Tris (Sigma-Aldrich: Trizma base) as a buffer. Ferritin and a nonionic surfactant were then added thereto to give 0.5 mg/mL and 1.0 v/v %, respectively. The nonionic surfactant employed was Tween 20 (ICI) represented by the following chemical formula 1.

[Chemical formula 1]

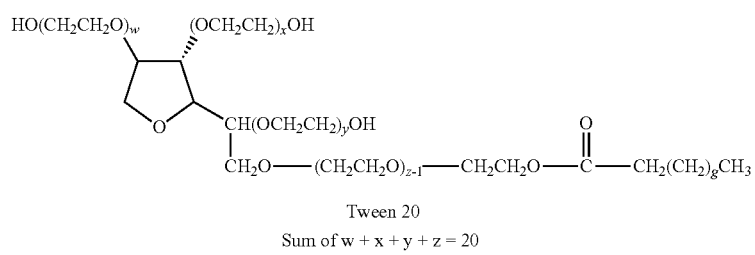

Tween 20

Sum of w + x + y + z = 20

<Binding Step>

The substrate cleaned as described above was placed in a 1 inch wafer tray, and thereto was added 100 μL of the prepared solution dropwise. Thereafter, the 1 inch wafer tray was covered with a lid in order to prevent from drying, and left to stand for 10 min. Thereafter, a step of adding 500 μL of the buffer solution alone dropwise thereto and removing 500 μL of thus diluted solution by aspiration was repeated three times. Then a similar step of adding 1 mL of ultra-pure water alone dropwise thereto, and removing 1 mL of the diluted solution by aspiration was repeated three times, followed by washing in a beaker with running ultra-pure water for 5 min. Finally, ultra-pure water was blown off to dry by a nitrogen flow.

<Electron Microscope (SEM) Observation>

On the substrate subjected to the binding step, inorganic particle cores contained in ferritin were observed using a high resolution electron microscope (JEOL: JSM-7400F) to determine the number of ferritin on the substrate. The number was counted after cutting away an area of a 200 nm×200 nm square from the SEM image. When the number was less than 100, an average of measurements at three points was derived.

Figure 3:
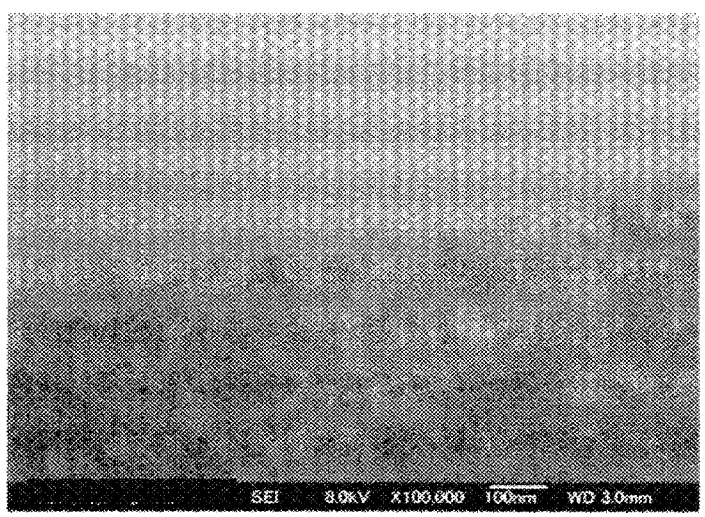
FIG. 3 shows a micrograph illustrating an SEM image of iron core-containing the minT1-LF arrayed on a silicon oxide substrate at a vanadium portion.
Figure 3:
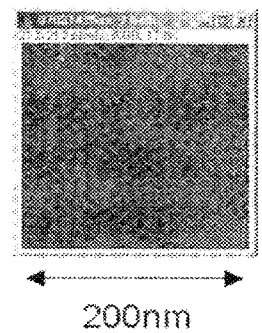
Figure 4:
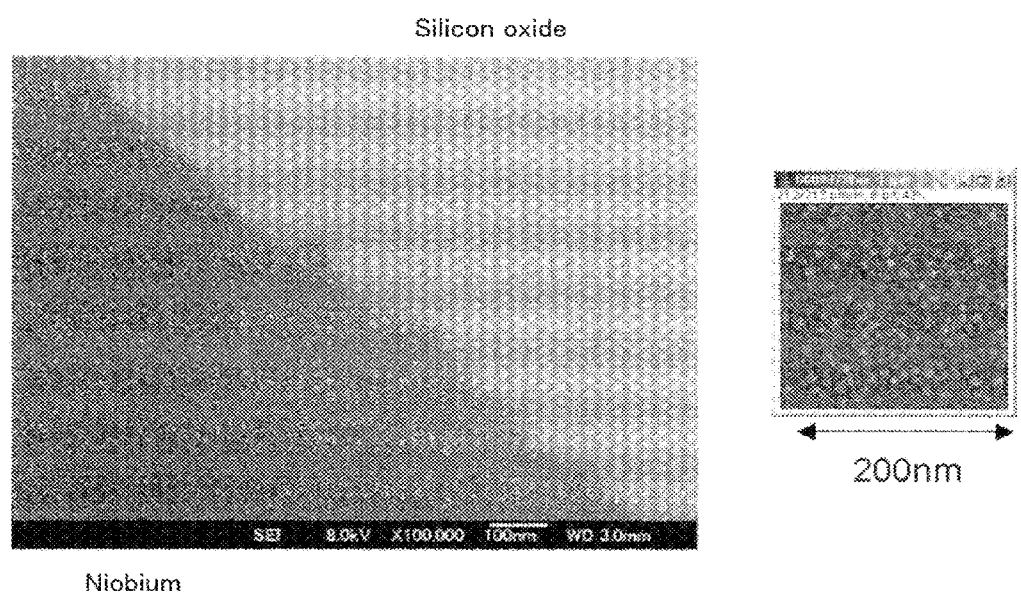
FIG. 4 shows a micrograph illustrating an SEM image of iron core-containing the minT1-LF arrayed on a silicon oxide substrate at a niobium portion.
Figure 5:
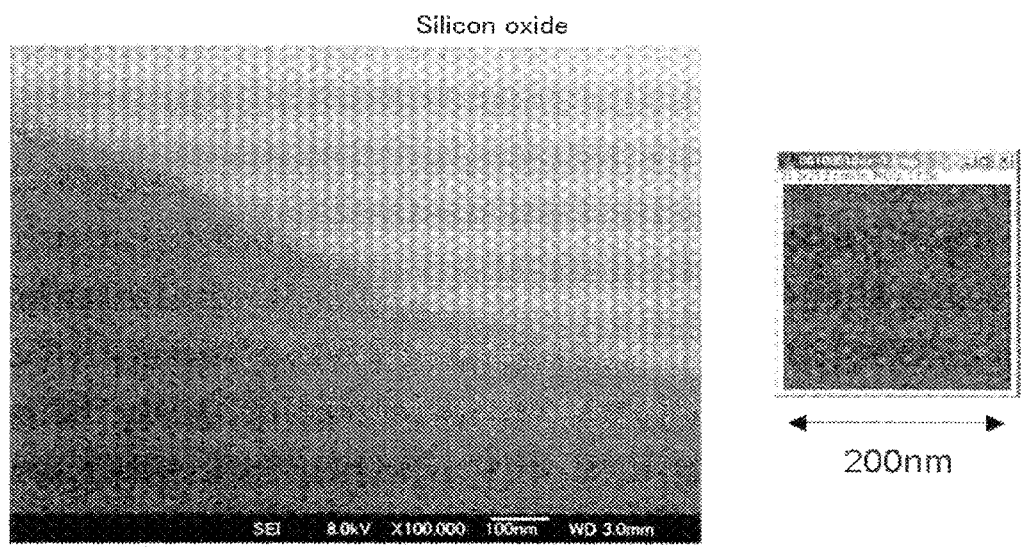
FIG. 5 shows a micrograph illustrating an SEM image of iron core-containing the minT1-LF arrayed on a silicon oxide substrate at a tantalum portion.

An SEM image of the minT1-LF arrayed on the silicon oxide at a vanadium portion, and an enlarged view of the vanadium portion are shown in FIG. 3. An SEM image of the minT1-LF arrayed on the silicon oxide at a niobium portion, and an enlarged view of the niobium portion are shown in FIG. 4. An SEM image of the minT1-LF arrayed on the silicon oxide at a tantalum portion, and an enlarged view of the tantalum portion on the silicon oxide are shown in FIG. 5. The minT1-LF is selectively arrayed on the vanadium, niobium, or tantalum portion. In the case of Δ1-LF, the number of array of the vanadium or niobium portion accounted for 50% of the minT1-LF, and the number of array of the tantalum portion accounted for no greater than 40% of the minT1-LF.

Example 2

50 mM MES-Tris prepared to have a pH each adjusted to 6.7, 7.4, 7.8, 8.0 and 8.2 were used as the buffer, and solutions were prepared having a ferritin concentration of 2.0 mg/mL and a nonionic surfactant (Tween 20) concentration of 1 v/v %.

Figure 6:
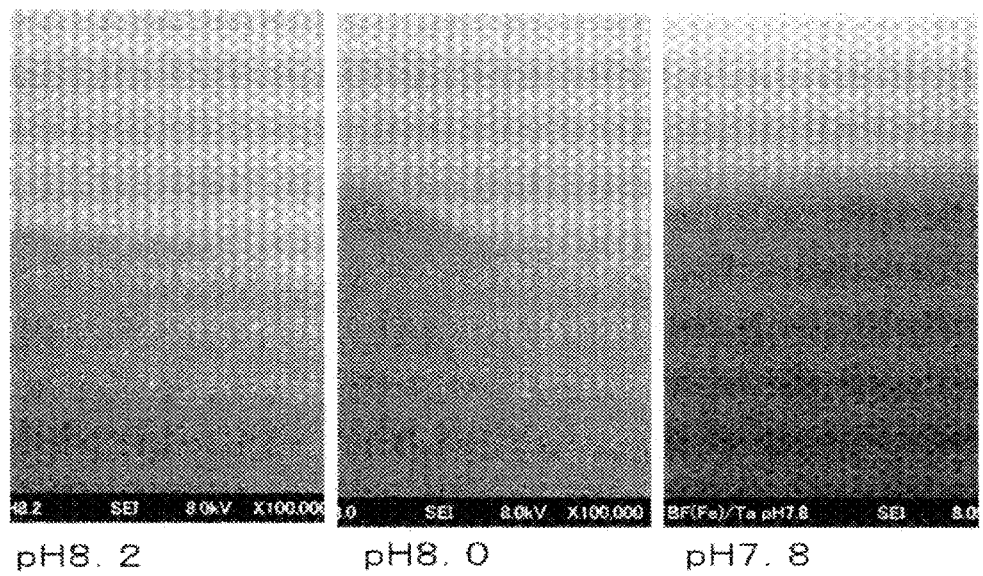
FIG. 6 shows a micrograph illustrating an SEM image of iron core-containing the minT1-LF arrayed on a silicon oxide substrate at a tantalum portion at varying pH.
Figure 7:
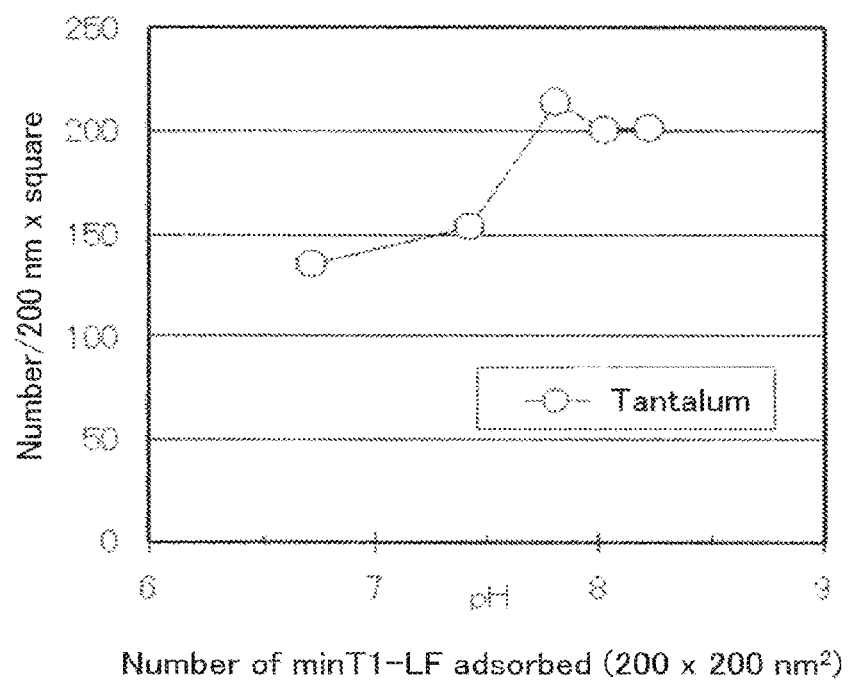
FIG. 7 shows a graph illustrating pH dependency of the number of adsorption of the minT1-LF.

Then, a binding step similar to that in Example 1 was carried out using this solution. SEM images of the substrate surface after the binding step are shown in FIG. 6, and the results of measurement of the number of the minT1-LF are shown in FIG. 7. When the pH was 7.4 or 6.7, the minT1-LF was likely to aggregate in the solution, and thus the solution became turbid immediately after mixing at pH 6.7, and after several minutes passed at pH 7.4. Thus, aggregates were frequently found also for the minT1-LF arrayed on the solid surface. Although the results of measurement for the portions other than the aggregates are shown in FIG. 7, it was difficult to obtain stable results at a pH lower than 7.4. It was necessary to complete the operation within a short period of time also at pH 7.4. Accordingly, the pH is preferably higher than 7.4 for readily obtaining stable results.

As shown in FIG. 7, the number of the minT1-LF arrayed at the tantalum portion was particularly large at a pH of from 8.2 to 7.8. Although the number decreased when the pH was below 7.4, favorable results taking into consideration the influence of the aggregation in the solution described above were obtained at a pH not less than 7.4, and preferably not less than 7.8.

Figure 8:
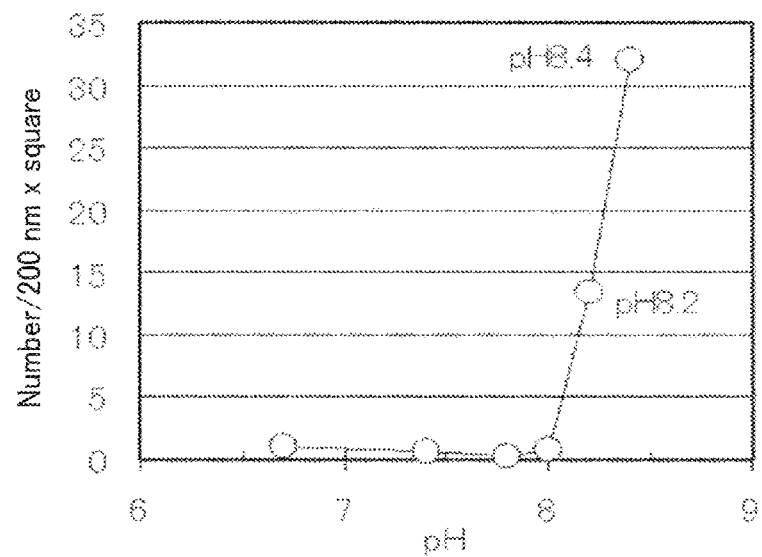
FIG. 8 shows a graph illustrating pH dependency of the number of adsorption of the minT1-LF on a silicon oxide substrate.
Figure 9:
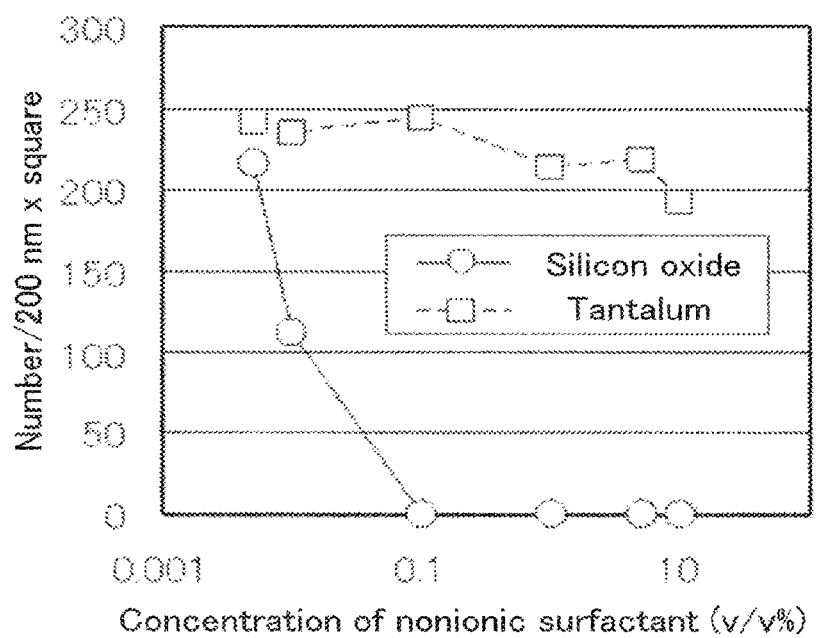
FIG. 9 shows a graph illustrating nonionic surfactant concentration dependency of the number of adsorption of the minT1-LF.

On the other hand, the number of array of the minT1-LF on the silicon oxide substrate is shown in FIG. 8. Since the number on the silicon oxide is small, an experiment of directly arraying on the silicon oxide substrate was conducted including the case at pH 8.4. At a pH of 6.7 to 8.2, the results were substantially similar to those of the substrates on the half surface having vanadium, niobium, or tantalum. In addition, the number of adsorption increased when the pH was higher than 8.2, in the alkaline region. Accordingly, it was suggested that ferritin was selectively arrayed at a vanadium, niobium, or tantalum portion at a pH of not greater than 8.2, and preferably not greater than 8.0.

The number of array of Δ1-LF according to the experimental results did not exceed 100 in a 200 nm×square within the pH range of from 6.7 to 8.2.

Influences of the protein concentration are summarized in Table 1 along with the results of Example 1; however the influences of protein concentration were negligible.

TABLE 1

|  | Protein concentration | |
|---|---|---|
|  | 0.5 mg/mL | 2.0 mg/mL |
| Vanadium | 270 | — |
| Niobium | 179 | — |
| Tantalum | 197 | 214 |
| Silicon oxide | 0.4 | 0.3 |

Number/200 nm × square
pH 7.8
Nonionic surfactant: 1 v/v %

Example 3

To a solution containing 50 mM MES-Tris (pH 7.8) as the buffer, and ferritin at a concentration of 0.5 mg/mL, was added a nonionic surfactant Tween 20 at each concentration of 0.005, 0.01, 0.1, 1, 5, 10, 15 and 20 v/v % to prepare solutions. These solutions were added to a silicon oxide/tantalum substrate dropwise, and subjected to the binding step.

The nonionic surfactant has a high viscosity, and is likely to form bubbles; therefore, reproducible results were not obtained when the concentration of the nonionic surfactant was 15 v/v % or 20 v/v %. The number of array of the minT1-LF was almost constant at a tantalum portion. On the silicon oxide substrate, the array number abruptly increased when the concentration was lower than 0.01 v/v %, and the number was almost the same as that on tantalum when the concentration was 0.005 v/v %. From the foregoing results, the minT1-LF achieved selectivity of array to the tantalum portion at a concentration of the nonionic surfactant of not less than 0.01 v/v %, and preferably not less than 0.1 v/v %.

Also when Tween 80 represented by the chemical formula 2 was used as a surfactant, similar result was obtained.

[Chemical formula 2]

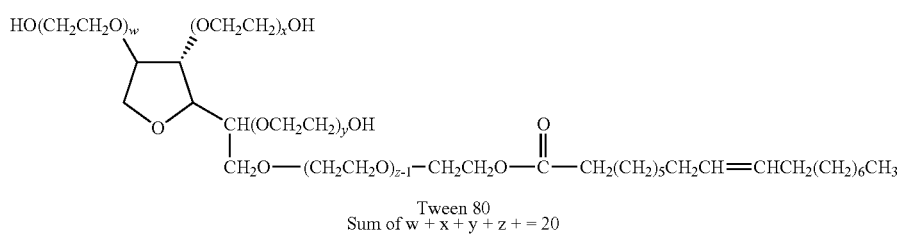

Tween 80
Sum of w + x + y + z + = 20

Example 4

A solution containing 50 mM MES-Tris (pH 7.8) as the buffer, ferritin at a concentration of 0.5 mg/mL, and 1 v/v % Tween 20 as a nonionic surfactant was prepared. This solution was added dropwise on a silicon oxide substrate (5 mm×10 mm) on which a tantalum thin line having a width of 20 nm and a length of 200 nm had been formed, and subjected to the binding step. In the removal step of the solution, the substrate was placed in a 1.5 mL Eppendorf tube, and centrifuged at 2,000 G to remove the solution. On the thin line, 2 to 3 molecules of the minT1-LF were arrayed on rows that run along the width direction. In addition, on the silicon oxide substrate, the minT1-LF was not found except for the end of the substrate and the vicinity of silicon waste piece.

In the cleaning step of the solution, the substrate after subjecting to the binding step was sequentially washed with a buffer and pure water, and the substrate surface was observed. Accordingly, on the thin line, one molecule of the minT1-LF was arrayed on rows that run along the width direction. In addition, the minT1-LF was not found on the silicon oxide substrate.

As in the foregoing, selective array of the minT1-LF at a nano dimension tantalum portion is enabled according to the present invention.

Similar results were obtained even when cobalt oxide was used in place of ferric oxide as the inorganic particles to be contained in ferritin. In the case of the minT1-LF containing indium oxide, accurate comparison of the number was difficult since indium oxide particles lose secondary electron emission resulting from irradiation with electron beam of SEM (speculated to be evaporated probably); however, almost similar results were obtained by simple calculation of the number with a low magnification.

From the foregoing description, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

INDUSTRIAL APPLICABILITY

The method of arraying ferritin according to the present invention enables ferritin and inorganic particle to be selective arrayed on a silicon oxide substrate at a vanadium, niobium, or tantalum portion.

Since tantalum is often used as a diffusion preventive layer and a substrate layer of a metal thin film, it is advantageous for use in applications of selective array of a slight amount of an inorganic element on an interface for the purpose of improving metal wiring interface.

Since vanadium and niobium are often used as a catalyst, it can be adopted in applications of efficiently forming a catalyst-catalytic promoter joint interface on a silicon oxide substrate in the case of catalysts composed of silicon oxide as a substrate and vanadium, niobium or tantalum is dispersed therein, by selectively arraying ferritin containing inorganic particles used as a catalytic promoter.

SEQUENCE LISTING

<110> Panasonic Corporation
<120> Arrangement Method of Ferritin
<130> P54202-P0
<150> JP 2009-122867
<151> 2009-5-21
<160> 5
<210> 1
<211> 6
<212> PRT
<213> Artificial Sequence
<400> 1
Arg Lys Leu Pro Asp Ala
1 5
<210> 2
<211> 528
<212> DNA
<213> Equus caballus
<400> 2
atgagctccc agattcgtca gaattattct actgaagtgg aggccgccgt caac-cgcctg 60
gtcaacctgt acctgcgggc ctcctacacc tacctctctc tgggcttcta tttc-gaccgc 120
gacgatgtgg ctctggaggg cgtatgccac ttcttccgcg agttggcgga ggagaagcgc 180
gagggtgccg agcgtctctt gaagatgcaa aaccagcgcg gcggccgcgc tctcttccag 240
gacttgcaga agccgtccca ggatgaatgg ggtacaaccc cagacgccat gaaagccgcc 300
attgtcctgg agaagagcct gaaccaggcc cttttggatc tgcatgccct gggt-tctgcc 360
caggcagacc cccatctctg tagcttcttg tctagccact tcctagacga ggag-gtgaaa 420
ctcatcaaga agatgggcga ccatctgacc aacatccaga ggctcgttgg ctc-ccaagct 480
gggctgggcg agtatctctt tgaaaggctc actctcaagc acgactaa 528
<210> 3
<211> 175
<212> PRT
<213> Artificial Sequence
<400> 3
Met Ser Ser Gln Ile Arg Gln Asn Tyr Ser Thr Glu Val Glu Ala Ala
1 5 10 15
Val Asn Arg Leu Val Asn Leu Tyr Leu Arg Ala Ser Tyr Thr Tyr Leu
20 25 30
Ser Leu Gly Phe Tyr Phe Asp Arg Asp Asp Val Ala Leu Glu Gly Val
35 40 45
Cys His Phe Phe Arg Glu Leu Ala Glu Glu Lys Arg Glu Gly Ala Glu
50 55 60
Arg Leu Leu Lys Met Gln Asn Gln Arg Gly Gly Arg Ala Leu Phe Gln
65 70 75 80
Asp Leu Gln Lys Pro Ser Gln Asp Glu Trp Gly Thr Thr Pro Asp Ala
85 90 95
Met Lys Ala Ala Ile Val Leu Glu Lys Ser Leu Asn Gln Ala Leu Leu
100 105 110
Asp Leu His Ala Leu Gly Ser Ala Gln Ala Asp Pro His Leu Cys Ser
115 120 125
Phe Leu Ser Ser His Phe Leu Asp Glu Glu Val Lys Leu Ile Lys Lys
130 135 140
Met Gly Asp His Leu Thr Asn Ile Gln Arg Leu Val Gly Ser Gln Ala
145 150 155 160
Gly Leu Gly Glu Tyr Leu Phe Glu Arg Leu Thr Leu Lys His Asp
165 170 175
<210> 4
<211> 30
<212> DNA
<213> Artificial Sequence
<400> 4
GATCCATGCG CAAACTTCCGG ATGCGAGCT 30
<210> 5
<211> 22
<212> DNA
<213> Artificial Sequence
<400> 5
CGCATCCGGA AGTTTGCGCA TG 22

SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Chemically synthesized

<400> SEQUENCE: 1

Arg Lys Leu Pro Asp Ala
1               5

<210> SEQ ID NO 2
<211> LENGTH: 528
<212> TYPE: DNA
<213> ORGANISM: Equus caballus

<400> SEQUENCE: 2

```
atgagctccc agattcgtca gaattattct actgaagtgg aggccgccgt caaccgcctg      60
gtcaacctgt acctgcgggc ctcctacacc tacctctctc tgggcttcta tttcgaccgc     120
gacgatgtgg ctctggaggg cgtatgccac ttcttccgcg agttggcgga ggagaagcgc     180
gagggtgccg agcgtctctt gaagatgcaa aaccagcgcg gcggccgcgc tctcttccag     240
gacttgcaga gccgtccca ggatgaatgg ggtacaaccc cagacgccat gaaagccgcc     300
attgtcctgg agaagagcct gaaccaggcc cttttggatc tgcatgccct ggttctgcc     360 caggcagacc cccatctctg tagcttcttg tctagccact tcctagacga ggaggtgaaa     420
ctcatcaaga gatgggcga ccatctgacc aacatccaga ggctcgttgg ctcccaagct     480
gggctgggcg agtatctctt tgaaaggctc actctcaagc acgactaa                528
```

<210> SEQ ID NO 3
<211> LENGTH: 175
<212> TYPE: PRT
<213> ORGANISM: Artificial Sequence
<220> FEATURE:
<223> OTHER INFORMATION: Chemically synthesized

<400> SEQUENCE: 3

Met Ser Ser Gln Ile Arg Gln Asn Tyr Ser Thr Glu Val Glu Ala Ala
1               5                   10                  15

Val Asn Arg Leu Val Asn Leu Tyr Leu Arg Ala Ser Tyr Thr Tyr Leu
            20                  25                  30

Ser Leu Gly Phe Tyr Phe Asp Arg Asp Asp Val Ala Leu Glu Gly Val
        35                  40                  45

Cys His Phe Phe Arg Glu Leu Ala Leu Leu Lys Arg Glu Gly Ala Glu
    50                  55                  60

Arg Leu Leu Lys Met Gln Asn Gln Arg Gly Gly Arg Ala Leu Phe Gln
65                  70                  75                  80

Asp Leu Gln Lys Pro Ser Gln Asp Glu Trp Gly Thr Thr Pro Asp Ala
                85                  90                  95

Met Lys Ala Ala Ile Val Leu Glu Lys Ser Leu Asn Gln Ala Leu Leu
            100                 105                 110

Asp Leu His Ala Leu Gly Ser Ala Gln Ala Asp Pro His Leu Cys Ser
        115                 120                 125

Phe Leu Ser Ser His Phe Leu Asp Glu Glu Val Lys Leu Ile Lys Lys
    130                 135                 140

Met Gly Asp His Leu Thr Asn Ile Gln Arg Leu Val Gly Ser Gln Ala
145                 150                 155                 160

Gly Leu Gly Glu Tyr Leu Phe Glu Arg Leu Thr Leu Lys His Asp
                165                 170                 175

<210> SEQ ID NO 4
<211> LENGTH: 30
<212> TYPE: DNA

```
<213> ORGANISM: Artificial Sequence
<220> FEATURE:
<223> OTHER INFORMATION: Chemically synthesized

<400> SEQUENCE: 4
gatccatgcg caaacttccg gatgcgagct                                        30

<210> SEQ ID NO 5
<211> LENGTH: 22
<212> TYPE: DNA
<213> ORGANISM: Artificial Sequence
<220> FEATURE:
<223> OTHER INFORMATION: Chemically synthesized

<400> SEQUENCE: 5
cgcatccgga agtttgcgca tg                                                22
```

The invention claimed is:

1. A method of arraying ferritin, the method comprising steps of:

a preparing step of preparing a solution which contains ferritin modified at an N-terminal of a subunit with a peptide set out in SEQ ID NO: 1, wherein a serine residue at the N-terminal of the subunit is bonded to an alanine residue of the peptide of SEQ ID NO: 1, and from 0.01 v/v % to 10 v/v % of a nonionic surfactant, wherein the solution has a pH falling within the range of from 7.4 to 8.2; and a binding step of bringing the solution in contact with a silicon oxide substrate having a metal portion of one metal selected from vanadium, niobium, and tantalum formed on a part of the surface so as to selectively bind the ferritin to the metal portion.

2. The method according to claim 1, further comprising after the binding step, a removal step of removing the solution to leave the ferritin selectively bound to the metal portion on the silicon oxide substrate.

3. The method according to claim 1, further comprising after the binding step, a cleaning step of washing the surface of the silicon oxide substrate with a solution not containing the ferritin so as to leave the ferritin selectively bound to the metal portion at the metal portion on the silicon oxide substrate.

4. The method according to claim 1, wherein the ferritin contains inorganic particles.

5. The method according to claim 4, further comprising after the binding step, a decomposing step of heating the silicon oxide substrate to decompose the ferritin to array the inorganic particles which had been contained in the ferritin at the metal portion on the silicon oxide substrate.

* * * * *